United States Patent [19]

Hill

[11] Patent Number: 5,709,017
[45] Date of Patent: Jan. 20, 1998

[54] TOOL FOR INSTALLING AN AIR VALVE ASSEMBLY

[76] Inventor: David A. Hill, P.O. Box 3843, Turlock, Calif. 95381-3843

[21] Appl. No.: 557,364

[22] Filed: Nov. 13, 1995

Related U.S. Application Data

[62] Division of Ser. No. 42,084, Apr. 1, 1993, Pat. No. 5,490,537.

[51] Int. Cl.$^6$ .................................................. B23P 19/04
[52] U.S. Cl. ............................................. 29/213.1; 29/240
[58] Field of Search .......................... 623/34, 27, 30, 623/33, 35, 37; 29/213.1, 263, 240; 81/176.1, 176.15, 221.6

[56] References Cited

U.S. PATENT DOCUMENTS

| | | | |
|---|---|---|---|
| 1,177,843 | 4/1916 | Ackerman et al. | 29/263 |
| 2,036,782 | 4/1936 | Ullmo | 29/263 |
| 2,641,052 | 6/1953 | Fennema et al. | 29/240 |
| 3,693,484 | 9/1972 | Sanderson | 81/176.15 |
| 3,815,209 | 6/1974 | Basile | 29/240 |
| 4,262,562 | 4/1981 | MacNeill | 81/176.15 |

*Primary Examiner*—Robert C. Watson

[57] ABSTRACT

An improved air valve assembly for mounting in a prosthesis, such as an artificial leg, and a spanner-type tool for mounting and removing the valve assembly. The valve assembly includes a housing to be mounted in the prosthesis with gaskets located on each side and secured therein by a removable retaining collar, a valve body removably mounted in the housing, and a spring-biased valve release stem mounted in the valve body, with seals positioned about the valve body and about the release stem. The spanner-type tool includes a spanner having protruding pins which are adapted to extend into holes in the valve housing and a threaded central opening into which is threaded a screw shaft which is adapted to extend through the valve housing, the screw shaft extending through a central opening in a tool body and handle and secured to a knob, and with a retainer ring mounted in a groove in the screw shaft and located intermediate the spanner and the tool body. The tool enables the valve housing to be held against the prosthesis, without rotation therein, while the retaining collar is being tightened so as to provide a firm installation of the valve housing and gaskets in the prosthesis.

11 Claims, 2 Drawing Sheets

TOOL FOR INSTALLING AN AIR VALVE ASSEMBLY

This is a Division of application Ser. No. 08/042,084 filed Apr. 1, 1993 now U.S. Pat. No. 5,490,539.

BACKGROUND OF THE INVENTION

The invention relates to artificial limbs, particularly to an improved air valve for a prosthesis, and more particularly to a spanner-type tool for installing the valve in a prosthesis.

A prosthesis, such as an artificial leg, includes an air release valve through which air is discharged when the leg stump is inserted into the socket of the prosthesis, the socket being designed to fit the stump in a snug, suction-like manner. Air trapped between the stump and the socket must be released to assure a proper fit.

The air valve assembly is generally located near the bottom of the prosthesis leg socket, and the socket is of a length and small size, in some cases, that it is difficult to properly install the valve assembly. The valve assemblies generally include a housing or member which extends through an opening in the prosthesis and is secured therein by a retainer, with a gasket located on each side of the prosthesis. When this housing is not properly installed, the gaskets do not seal properly and allow air leakage into the socket. Also, many of the conventional valve housings include an outer edge configuration which is designed to cooperate with a mating configuration on the inner surface of the socket to prevent the housing from turning during installation. In many instances the housing is not properly seated in the mating configuration of the socket, which allows the housing to turn when the retainer is tightened, whereby the gaskets fail to provide a proper fit around the opening in the socket of the prosthesis.

A need has existed for method or means by which the valve housing can be properly installed in a prosthesis so as to assure no air leakage. This need is satisfied by the present invention which includes an improved prosthesis valve assembly and a tool for installing the valve assembly housing in a prosthesis socket, whereby the problem of air leakage is eliminated.

SUMMARY OF THE INVENTION

An object of the present invention is to provide a means by which a hollow member can be installed in an opening in another member and retained therein so as to prevent leakage of air therebetween.

A further object of the invention is to provide an improved air valve assembly and tool for installing same.

It is a further object of the invention to provide a spanner-type tool for installing hollow members in an opening.

Another object of the invention is to provide an improved air valve assembly for a prosthesis and a spanner-type tool for installing the valve assembly in a prosthesis.

Another object of the invention is to provide a spanner-type tool for installing a valve housing in an opening in a prosthesis whereby gaskets are seated so as to prevent air leakage around the housing.

Still another object of the invention is to provide a tool and a prosthesis air valve assembly including a housing designed for installation and retention in an opening in the prosthesis such that the housing does not turn during installation thereby assuring proper seating of gaskets for preventing air leakage into the prosthesis.

Other objects and advantages of the invention will become apparent from the following description and accompanying drawings. Basically the invention involves a tool for installing a member having a passageway extending therethrough in an opening whereby the member is prevented from turning during installation. More specifically the invention involves a spanner-type tool for installing a member, such as a valve housing of a prosthesis, in an opening in the prosthesis which provides for proper seating of gaskets to prevent air leakage into the prosthesis. Specifically, the invention is directed to a combination of an improved prosthesis air valve housing and a spanner-type or rotational-biasing tool or wrench for installing the valve housing in an opening in a socket of the prosthesis, whereby gaskets located about both sides of the socket opening are properly seated for preventing air passage through the opening.

DETAILED DESCRIPTION OF THE INVENTION

The present invention is broadly directed to the combination of spanner-type or rotational-biasing tool or wrench and an improved flanged housing or member and retaining collar. The flanged housing is adapted to be mounted and retained by a retainer or collar in an opening, via the spanner-type tool, such that the housing does not rotate during installation and the flanged portion thereof functions to properly seat and retain a gasket about one side of the opening. The retaining collar is designed to properly seat and retain a gasket about the opposite side of opening while retaining the flanged housing therein. As a result of the proper seating of the gaskets, air leakage through the opening is prevented.

While the spanner-type tool and/or the flanged housing/retainer assembly designed to cooperate with the tool may be utilized in any application requiring non-rotation or turning of the housing during installation, such as in various relatively inaccessible or pocket type applications, the following description is directed to an application of the invention for the installation of an air valve assembly in a socket of a prosthesis. Here the flanged housing/retainer assembly includes a removable air valve with a poppet assembly therein, the air valve being removed during installation of the housing/retainer by the spanner-type tool.

Figure 1:
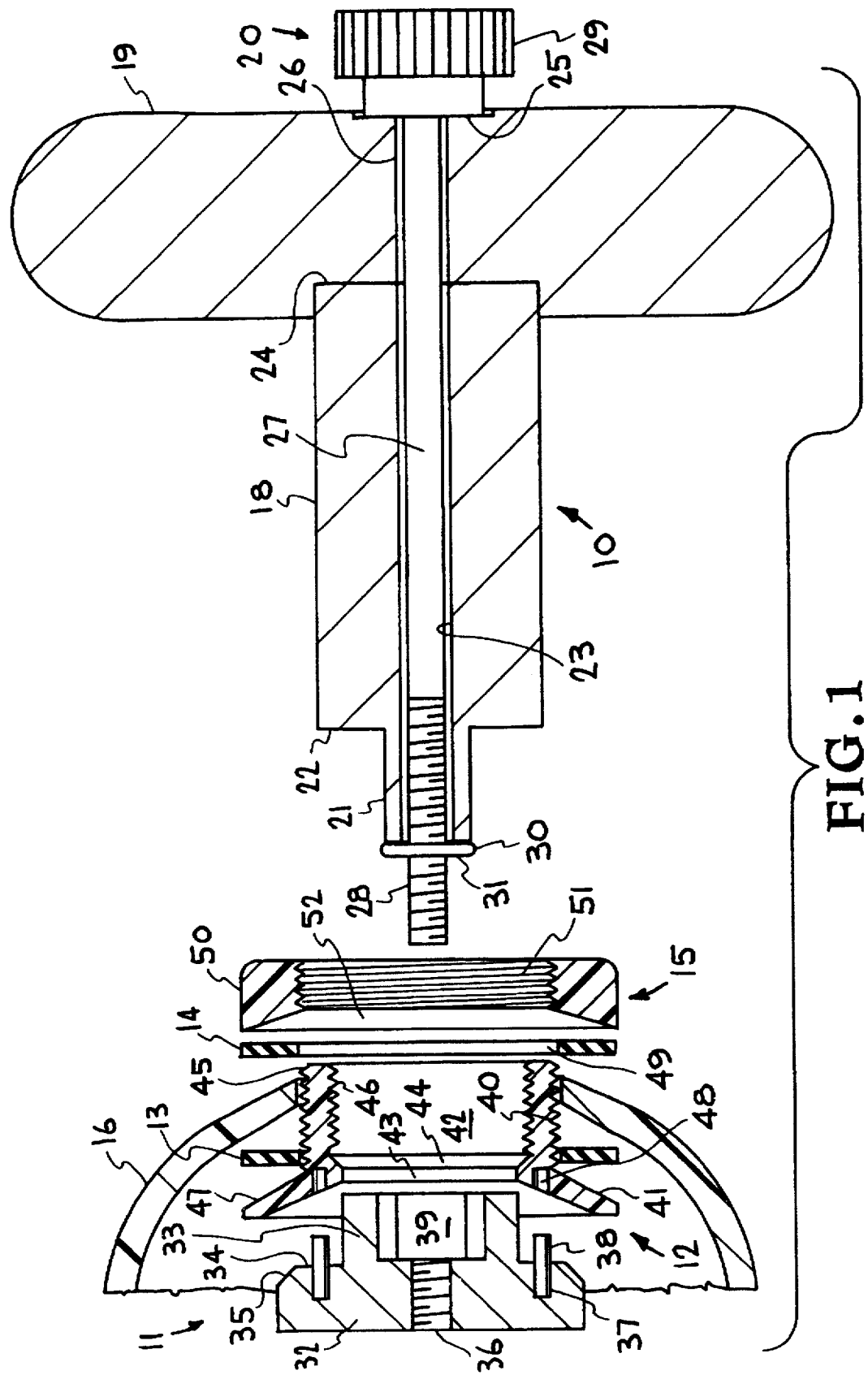
FIG. 1 is an exploded view of an embodiment of the spanner-type tool and an embodiment of an improved air valve housing, each made in accordance with the invention, positioned in an opening in a prosthesis socket.
Figure 2:
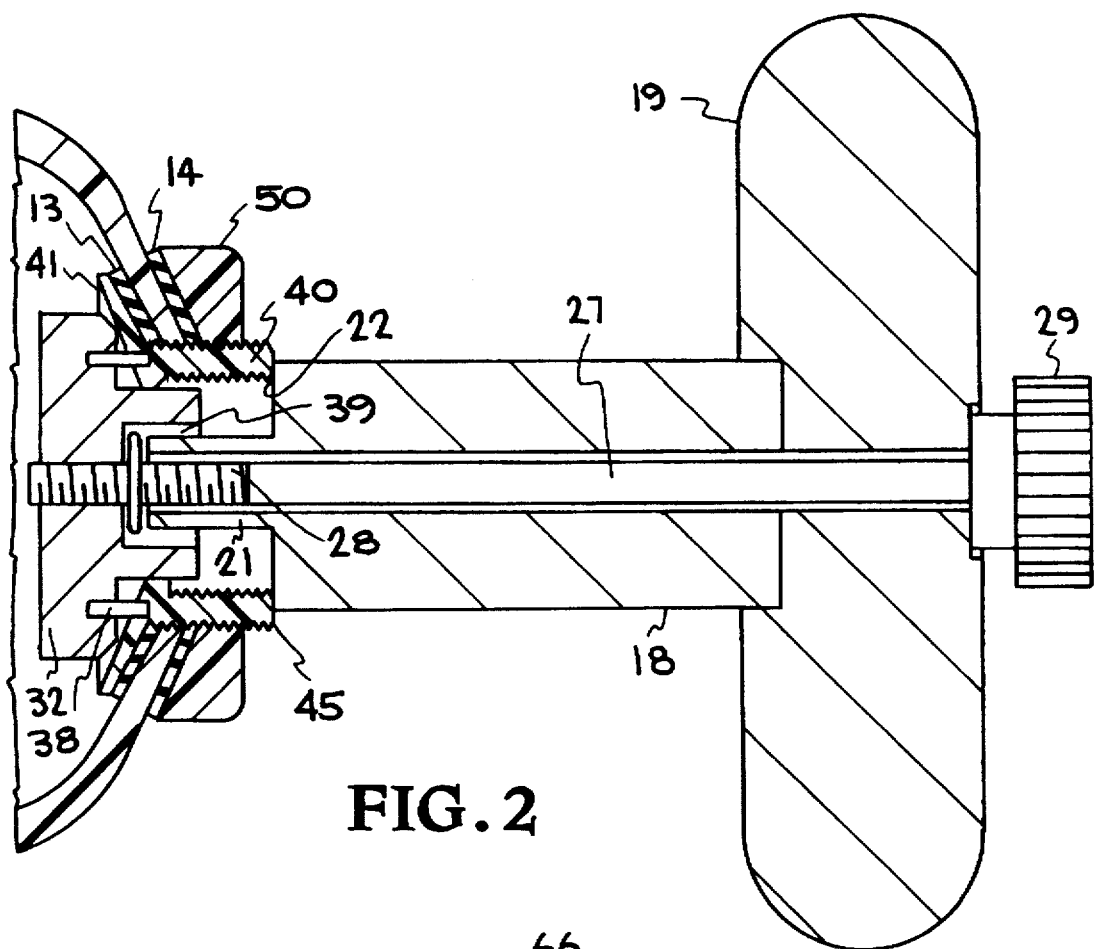
FIG. 2 illustrates the tool and valve housing of FIG. 1 with the valve housing in its installed position in the prosthesis socket.
Figure 3:
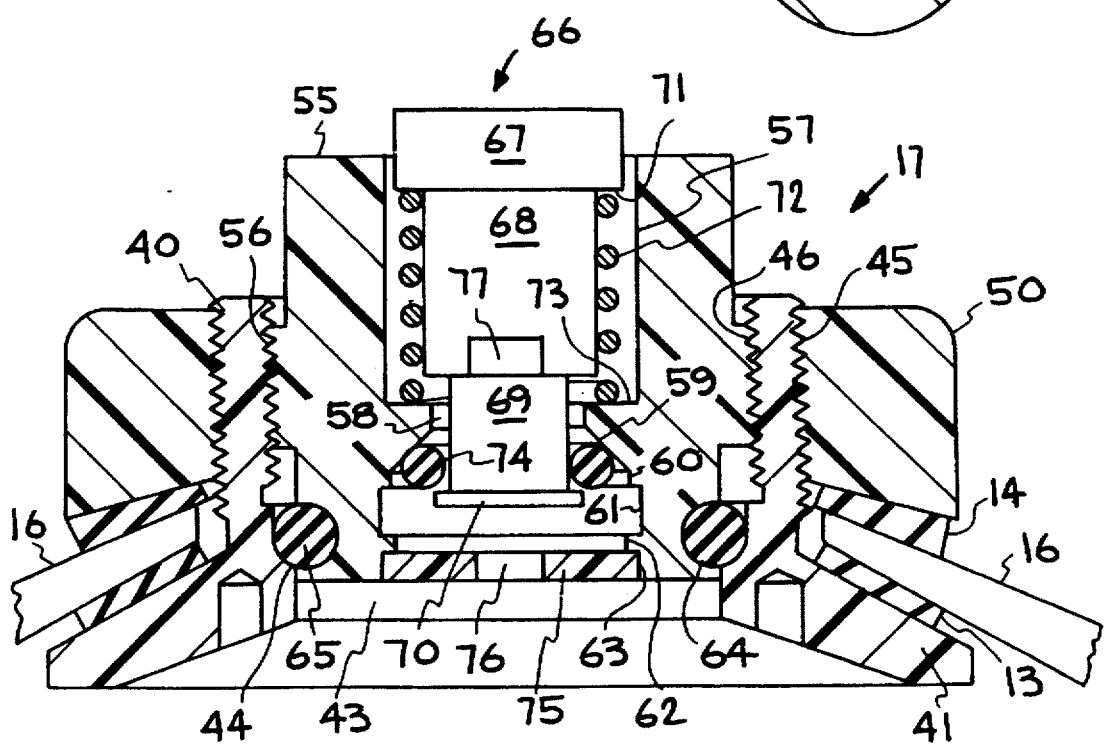
FIG. 3 illustrates an embodiment of the improved prosthesis air valve assembly of this invention.

Referring now to the drawings, the illustrated embodiment of the spanner-type tool and housing/retainer assembly comprises, as shown in FIG. 1, a spanner tool body section generally indicated at 10, a spanner generally indicated at 11, a flanged housing generally indicated at 12, a pair of gaskets 13 and 14, a retainer or collar generally indicated at 15, and a portion of a prosthesis socket 16, with a valve assembly generally indicated at 17 mounted in housing 12, as shown in FIG. 3. FIG. 2 illustrates the tool and housing/retainer assembly of FIG. 1 in its as installed position, prior to removal of the tool. The spanner tool body section 10 and the spanner 11 may be fabricated from any desirable metal and/or plastic having sufficient strength to withstand the pressures applied during installation of the housing/retainer assembly. The flanked housing 12, gaskets 13 and 14, and retainer or collar 15 may be fabricated from plastic and/or rubber which is machinable or moldable and with the chemical make-up and physical characteristics capable of withstanding installation and extended use. The prosthesis socket 16 may be a conventional thermal-plastic suction socket such as used in artificial legs, for example.

Referring now to FIG. 1, the tool body section 10 comprises a body member 18, a handle 19, and a screw assembly generally indicated at 20. Body member 18 includes a protruding end section 21 of reduced cross-section defining therebetween a shoulder 22 and having a central longitudinally extending opening or passage 23. Handle 19 is provided with cut-away sections 24 and 25 on opposite sides and an opening or passage 26 extending therebetween. Handle 19 is mounted on body member 18 via cut-away 24 such that passages 23 and 25 are aligned, and may be secured to body member 18, as by welding, bonding or screws, not shown. Screw assembly 20 comprises a shaft 27 threaded at one end 28 and secured at the opposite end to a knob or turning mechanism 29. Shaft 27 extends through passages 23 and 26 in body member 18 and handle 19 and is secured therein by a retainer or ring 30 positioned in a groove, not shown but indicated at 31, in shaft 27, such that knob 29 is retained in cut-away 25 of handle 19.

Spanner 11 comprises a body or member 32 having a protruding section 33 of reduced cross-section forming a shoulder 34 therebetween, a tapered or curved edge 35 adjacent shoulder 34, and a central threaded opening 36. Body 32 is also provided with a plurality of holes 37 extending inward from shoulder 34 and in which are secured pins 38. Protruding end section 33 is provided with a centrally located counter-sink 39 into which end section 21 and retainer or ring 30 of tool body section 10 extend when threaded end 28 of tool body section 10 is threaded into threaded opening 36 of spanner body 32, as seen in FIG. 2.

Flanged housing 12 comprise a body section 40 and an outwardly extending flange section 41 at one end of the body section, and through which extends an opening having different diameter portions 42 and 43 interconnected by a tapered portion 44. Body section 40 is provided with external threads 45 and internal threads 46 on the opening portion 42. As seen, flange section 41 extends from body section 40 in both radial and longitudinal directions and has an outwardly tapering surface 47. Also flange section 41 includes a plurality of holes 48 into which pins 38 of spanner 11 are inserted during installation, as seen in FIG. 2. The configuration and taper, if any, of the flange section 41 would depend on the inner surface configuration of the prosthesis socket 16 in which the flanged housing 12 is being inserted. The purpose of the flange section 41 is to properly seat the gasket 13 against the inner surface of the socket 16 as seen in FIGS. 2 and 3.

Gaskets 13 and 14 include openings 49 through which extend the body section 40 of flanged housing 12.

Retainer or collar 15 includes a body 50 having a threaded opening 51 and a concave or inwardly tapering surface 52. The configuration of the surface 52 will depend on the curvature or outer surface configuration of the prosthesis socket 16. The tapering surface 52 may be omitted if the surface of the prosthesis 16 is flat. The purpose of the surface 52 of collar 15 is to properly seat the gasket 14 against the outer surface of the socket 16, as seen in FIGS. 2 and 3.

To install the flanged housing 12 in prosthesis socket 16 with gasket 13 therebetween, and retain same therein by collar 15, the body 32 of spanner 11 is attached via pins 38 and holes 48 to flange section 41, with the protruding end section 33 of body 32 extending into openings 42–44 in body section 40 of housing 12. The body 18 of tool section 10 is inserted through collar 15 and gasket 14, with threaded end 28 of shaft 27 and body end section 21 extending into openings 42–44, whereby end 28 is threaded into threaded opening 36 of spanner body 32 via turning the knob 29 of tool section 10. Turning of knob 29 causes the tool body 18 to contact the end of body section 40 of housing 12 at shoulder 22, whereafter continued turning of knob 29 snugs the spanner 11 against the housing 12 and holds same from turning via pins 38. Whereafter the gasket 14 is positioned against the outer surface of socket 16. Gasket 14 may have an internal diameter which will require threading thereof on external threads 45 of housing body section 40. The collar 15 is then threaded on housing 12 via threaded opening 51 and threads 45 of the housing body, and tightened so as to cause gaskets 13 and 14 to compress against the opposite sides of prosthesis socket 16, as shown in FIGS. 2 and 3. As seen in FIGS. 2 and 3, this produces a flat sealed surface between the inner surface socket 16 and flange section 41 of housing 12 and between the outer surface of socket 16 and surface 52 of collar 15, thereby preventing air leakage therebetween.

Upon installation of the flanged housing 12, gaskets 13 and 14, and collar 15, as shown in FIG. 2, the spanner tool section 10 is removed from spanner 11 by rotating the knob 29 in the opposite direction, whereby the threaded end 28 of tool section 10 is withdrawn from the threaded opening 36 in spanner 11, leaving the flanged housing 12 secured in socket 16, for insertion of the air valve assembly 17 therein, see FIG. 3.

The embodiment of the air valve assembly of FIG. 3 comprises a valve body 55 having an external threaded section 56 by which the valve body is threaded into body section 40 of flanged housing 12 via internal threads 46. Valve body 55 also includes a central opening of differing cross-sections indicated at 57, 58, 59, 60, 61, 62 and 63, with opening sections 60 and 62, and sections 61 and 63 being of the same cross-section. Also valve body 55 includes a groove 64 in which a seal 65, such as an o-ring, is retained and which contacts the tapered surface forming opening 44 in flanged housing 12. A spring-biased poppet, generally indicated at 66, is mounted in the central opening of valve body 55 and comprises a body member having portions or sections of different cross-sections indicated at 67, 68, 69 and 70. Portions 67 and 68 define a shoulder 71, and a spring 72 is positioned between between shoulder 71 and a shoulder 73 formed between sections 57 and 58 of the central opening of valve body 55. Positioned around section 69 of the poppet body member is a seal 74, such as an o-ring, which provides a sealing action, when the poppet valve 66 is in its non-activated position (spring-biased outwardly), between the tapered surface of opening section 59 and poppet body section 70, but releases the sealing action when the poppet body is pressed inwardly against the pressure of spring 72 due to the tapered configuration of the opening section 59 and the length of the poppet body section 69. A plug or member 75 having an opening 76 is located in opening section 63 of the valve body 55.

In its non-activated position, as shown in FIG. 3, the poppet valve 66 is in its spring-biased or closed position via seal 74. By pushing inwarrdly (downwardly as shown) on the body section 67 of poppet valve 66, the pressure or force of spring 72 is overcome and the poppet body moves inward whereby the sealing action of seal 74 is removed and air from within prosthesis socket 16 is allowed to exit through the opening 76 in plug 75 and through the central opening sections 63–57 of valve body 55. The poppet body is constructed so that inward movement thereof is stopped when body section 68 contacts shoulder 73 of valve body 55. To prevent blockage of air passage when the poppet valve is in its innermost stopped position against shoulder 73, a plurality of notches 77 (only one shown) are provided in poppet body section 68 adjacent body section 69, to function as air bleeds or passageways, whereby air my continue to exit with the poppet body at its innermost or stopped position.

It has been shown that the present invention provides an improved flanged housing/retainer assembly and spanner-type tool for installing same. Also, the invention provides a means for eliminating the air leakage problems relating to prosthesis sockets, as well as providing an installation tool and improved air valve assembly for such sockets.

While a particular embodiment of the invention in an application for air valves in a prosthesis socket has been described to illustrate the principles of the invention, such is not intended to be limiting. Modifications and changes, as well as various uses, will become apparent to those skilled in the art, and it is intended that the scope of the invention be limited only by the scope of the appended claims.

I claim:

1. A tool for mounting a housing having an opening therein in an opening of a member such as a prosthesis socket, comprising:
    a spanner member having an opening therein, and at least one pin extending therefrom for contact with a housing to be mounted, and
    a spanner tool body adapted to be removably connected to said spanner member, said tool body including a rotatable shaft having one end section constructed to be removably connected to said spanner member,
    said spanner tool body additionally including a body member and a handle, each having a passage extending therethrough, said rotatable shaft extending through said passage and provided with shaft retaining means adjacent one end of said body member and a knob-like means secured to another end section.

2. The tool of claim 1, wherein said one end of said body member is of a lesser cross-section than the remainder thereof, wherein said one end section of said shaft is threaded, and wherein said spanner member includes a threaded section in said opening therein, whereby said one end of said body member extends into said opening in said spanner member when said threaded end section of said shaft is threaded into said threaded section of said opening in said spanner member such that threading said shaft into said spanner member causes said spanner member to be moved toward said spanner tool body for retaining an associated housing therebetween for mounting such an associated housing in an opening of an associated member such as a prosthesis socket.

3. A tool for installing a valve assembly in an opening, comprising:
    a spanner member having an opening therein, and means thereon adapted to contact and retain a member of an associated valve assembly to be installed; and
    a spanner tool body adapted to be removably connected to said spanner member,
    said spanner tool body including a body member and a handle, said body member having a passage extending therethrough, a rotatable shaft extending through said passage and having an end section operatively connected to said handle, and means adjacent one end of said body member for retaining said rotatable shaft in said body member.

4. The tool of claim 3, wherein said rotatable shaft of said spanner tool body includes another end section constructed to extend into said opening in said spanner member and be removably connected to said spanner member.

5. The tool of claim 4, wherein said opening in said spanner member includes a threaded section, and wherein said one end section of said rotatable shaft of said spanner tool body is provided with threads which cooperate with said threaded section of said opening in said spanner member for moving said spanner member toward said spanner tool body.

6. The tool of claim 3, wherein said means on said spanner member comprises at least one pin extending therefrom adapted to contact and retain a member of an associated valve assembly.

7. The tool of claim 3, wherein said handle includes an opening therethrough, said another end section of said rotatable shaft extending through said opening in said handle and connected to a knob-like means operatively mounted to said handle.

8. A tool for installing a valve assembly in an opening, comprising:
    a spanner member having an opening, and means thereon adapted to contact and retain a member of an associated valve assembly to be installed; and
    a spanner tool body adapted to be removably connected to said spanner member,
    said valve assembly comprising a valve housing assembly adapted to be mounted in an opening of a prosthesis socket, and a valve adapted to be removably mounted in said valve housing assembly,
    said valve housing assembly including a flanged housing having an opening therein and having a section thereof adapted to extend through an opening in the prosthesis socket,
    said valve housing assembly additionally including a retainer member adapted to be removably connected to said section of said flanked housing for retaining same in an opening in the prosthesis socket,
    said means on said spanner member being adapted to contact and retain said flanged housing of said valve housing assembly while said retainer member is moved to retain the flanged housing in an opening in the prosthesis socket.

9. The tool of claim 8, wherein said means on said spanner member comprises a plurality of outwardly extending members, and wherein said flanged housing is provided with a plurality of holes into which said outwardly extending members extend to retain said flanged housing from turning while said spanner tool pulls, via said spanner member, said flanged housing through and retains same in an opening in the prosthesis socket until said flanged housing is secured in the opening by said retainer member.

10. The tool of claim 9, wherein said valve housing assembly includes a gasket means adapted to be located intermediate said flanged housing and an associated prosthesis socket, whereby said gasket means is compressed when said spanner tool pulls said spanner member causing said flanged housing to be retained in an opening of the prosthesis socket.

11. The tool of claim 10, wherein said valve housing assembly includes another gasket means adapted to be located intermediate said retainer member and an associated prosthesis socket, whereby said another gasket means is compressed when said retainer member secures said flanged housing in an opening of an associated prosthesis socket.

* * * * *